US012478519B2

(12) United States Patent
Bajema

(10) Patent No.: US 12,478,519 B2
(45) Date of Patent: Nov. 25, 2025

(54) BI-DIRECTIONAL PACKAGING ADHESIVE

(71) Applicant: BEST BANDAGE, LLC, Spokane, WA (US)

(72) Inventor: Brett E. Bajema, Priest River, ID (US)

(73) Assignee: BEST BANDAGE, LLC, Spokane, WA (US)

( * ) Notice: Subject to any disclaimer, the term of this patent is extended or adjusted under 35 U.S.C. 154(b) by 0 days.

(21) Appl. No.: 18/818,258

(22) Filed: Aug. 28, 2024

(65) Prior Publication Data

US 2024/0415709 A1 Dec. 19, 2024

Related U.S. Application Data

(62) Division of application No. 17/883,995, filed on Aug. 9, 2022, now Pat. No. 12,097,105.

(60) Provisional application No. 63/334,293, filed on Apr. 25, 2022, provisional application No. 63/231,913, filed on Aug. 11, 2021.

(51) Int. Cl.
*A61F 15/00* (2006.01)

(52) U.S. Cl.
CPC .......... *A61F 15/002* (2013.01); *A61F 15/005* (2013.01)

(58) Field of Classification Search
CPC .................. A61F 15/002; A61F 15/005; A61F 13/00076; B65D 75/30; B65D 75/5805; B65D 75/5855; B65B 9/02; B65B 51/02; B65B 61/18
USPC .................................... 206/440–441; 602/57
See application file for complete search history.

(56) References Cited

U.S. PATENT DOCUMENTS

| | | | |
|---|---|---|---|
| 3,612,265 | A | 10/1971 | Dickerson |
| 4,235,337 | A | 11/1980 | Dotta |
| 4,265,234 | A | 5/1981 | Schaar |
| 4,781,293 | A | 11/1988 | Johns |

(Continued)

FOREIGN PATENT DOCUMENTS

| | | | |
|---|---|---|---|
| KR | 20200002200 | U | 10/2020 |
| WO | 2024035402 | A1 | 2/2024 |

OTHER PUBLICATIONS

U.S. Appl. No. 17/883,995, filed May 23, 2024 , "Notice of Allowance", U.S. Appl. No. 17/883,995, filed May 23, 2024, 9 pages.

(Continued)

*Primary Examiner* — Orlando E Aviles
*Assistant Examiner* — Brijesh V. Patel
(74) *Attorney, Agent, or Firm* — FIG. 1 Patents

(57) ABSTRACT

In aspects of bi-directional packaging adhesive, a sterile package includes a bandage with a sterile pad, and the bandage adheres to an applied surface. The sterile package includes a non-stick backing that adheres to the bandage, with the non-stick backing being removable for application of the bandage. The sterile package includes packaging that encompasses the bandage and the non-stick backing, and includes a bi-directional adhesive configured to release in a first package opening direction to remove the packaging while maintaining the adherence of the non-stick backing to the bandage, and hold in a second package opening direction to remove the non-stick backing from the bandage along with removing the packaging. A portion of the non-stick backing is attached to an inside of the packaging with the bi-directional adhesive, and the attached portion peels the non-stick backing from the bandage in the second package opening direction to open the packaging.

20 Claims, 11 Drawing Sheets

(56) References Cited

U.S. PATENT DOCUMENTS

| | | | |
|---|---|---|---|
| 4,915,228 | A | 4/1990 | Johns |
| 5,397,297 | A | 3/1995 | Hunter |
| 5,413,567 | A | 5/1995 | Barth et al. |
| 5,501,661 | A | 3/1996 | Cartmell et al. |
| 5,673,421 | A | 9/1997 | Shirakawa |
| 5,685,833 | A | 11/1997 | Turngren |
| 5,891,078 | A | 4/1999 | Turngren et al. |
| 5,981,823 | A | 11/1999 | Torngren |
| 6,124,522 | A | 9/2000 | Schroeder |
| 6,923,320 | B2 | 8/2005 | Grossman |
| 7,523,821 | B2 | 4/2009 | Assie et al. |
| 7,732,656 | B2 | 6/2010 | Stapf et al. |
| 8,251,213 | B2 | 8/2012 | Okada et al. |
| 8,561,796 | B2 | 10/2013 | Hatanaka et al. |
| 12,097,105 | B2 | 9/2024 | Bajema |
| 2004/0004014 | A1 | 1/2004 | Grossman |
| 2006/0151347 | A1 | 7/2006 | Grossman |
| 2009/0216169 | A1 | 8/2009 | Hansen et al. |
| 2011/0143133 | A1 | 6/2011 | Kinigakis et al. |
| 2011/0253304 | A1 | 10/2011 | Ohta et al. |
| 2012/0197173 | A1 | 8/2012 | Babitz |
| 2014/0116907 | A1 | 5/2014 | Holstein |
| 2014/0158572 | A1 | 6/2014 | Jensen |
| 2014/0231292 | A1 | 8/2014 | Miyachika et al. |
| 2014/0246144 | A1 | 9/2014 | Miyachika et al. |
| 2014/0303574 | A1 | 10/2014 | Knutson |
| 2023/0046409 | A1 | 2/2023 | Bajema |

OTHER PUBLICATIONS

U.S. Appl. No. 17/883,995, filed Jan. 31, 2024 , "Restriction Requirement", U.S. Appl. No. 17/883,995, filed Jan. 31, 2024, 5 pages.

PCT/US22/39978 , "International Search Report and Written Opinion", PCT Application No. PCT/US22/39978, Nov. 7, 2022, 68 pages.

"EP Search Report", EP Application No. 22955164.3, Jun. 2, 2025, 8 pages.

BI-DIRECTIONAL PACKAGING ADHESIVE

RELATED APPLICATIONS

This application is a divisional of and claims priority to U.S. patent application Ser. No. 17/883,995 filed Aug. 9, 2022 entitled "Bi-Directional Packaging Adhesive", the disclosure of which is incorporated by reference herein in its entirety. The U.S. patent application Ser. No. 17/883,995 claims priority to U.S. Provisional Patent Application Ser. No. 63/231,913 filed Aug. 11, 2021 entitled "Bi-Directional Packaging Adhesive", the disclosure of which is incorporated by reference herein in its entirety. The U.S. patent application Ser. No. 17/883,995 also claims priority to U.S. Provisional Patent Application Ser. No. 63/334,293 filed Apr. 25, 2022 entitled "Bi-Directional Packaging Adhesive", the disclosure of which is incorporated by reference herein in its entirety.

BACKGROUND

Generally, most bandages and adhesive patches can be difficult to open and apply, particularly while attempting to maintain sterility by not touching the sterile pad or the adhesive strip of a bandage or adhesive patch. Traditional bandages require several steps to open and remove the packaging, remove the two non-stick backing pieces, and then apply the bandage. Given that bandages are primarily used to cover an injury and/or stop blood flow, the simple act of opening a bandage packaging and applying the bandage can take much longer than is preferred. Additionally, this multiple-step process to open a bandage packaging and apply the bandage can result in several instances of contaminating the sterile pad and the adhesive strip in a non-sterile environment and inadvertent contact. In a medical setting in particular, this poses a contamination risk for a patient when a healthcare practitioner is challenged to apply a bandage without touching the adhesive portion of the bandage. Notably, touching the adhesive portion of the bandage can lead to a higher risk of infection or cross contamination across patients when a contaminated portion of the bandage is applied to a patient's skin. Additionally, traditional bandage packaging generally results in several individual pieces of the packaging and non-stick backing that a person has to then collect and dispose of after applying a bandage.

BRIEF DESCRIPTION OF THE DRAWINGS

Implementations of the techniques for bi-directional packaging adhesive are described with reference to the following Figures. The same numbers may be used throughout to reference like features and components shown in the Figures.

DETAILED DESCRIPTION

Figure 1:
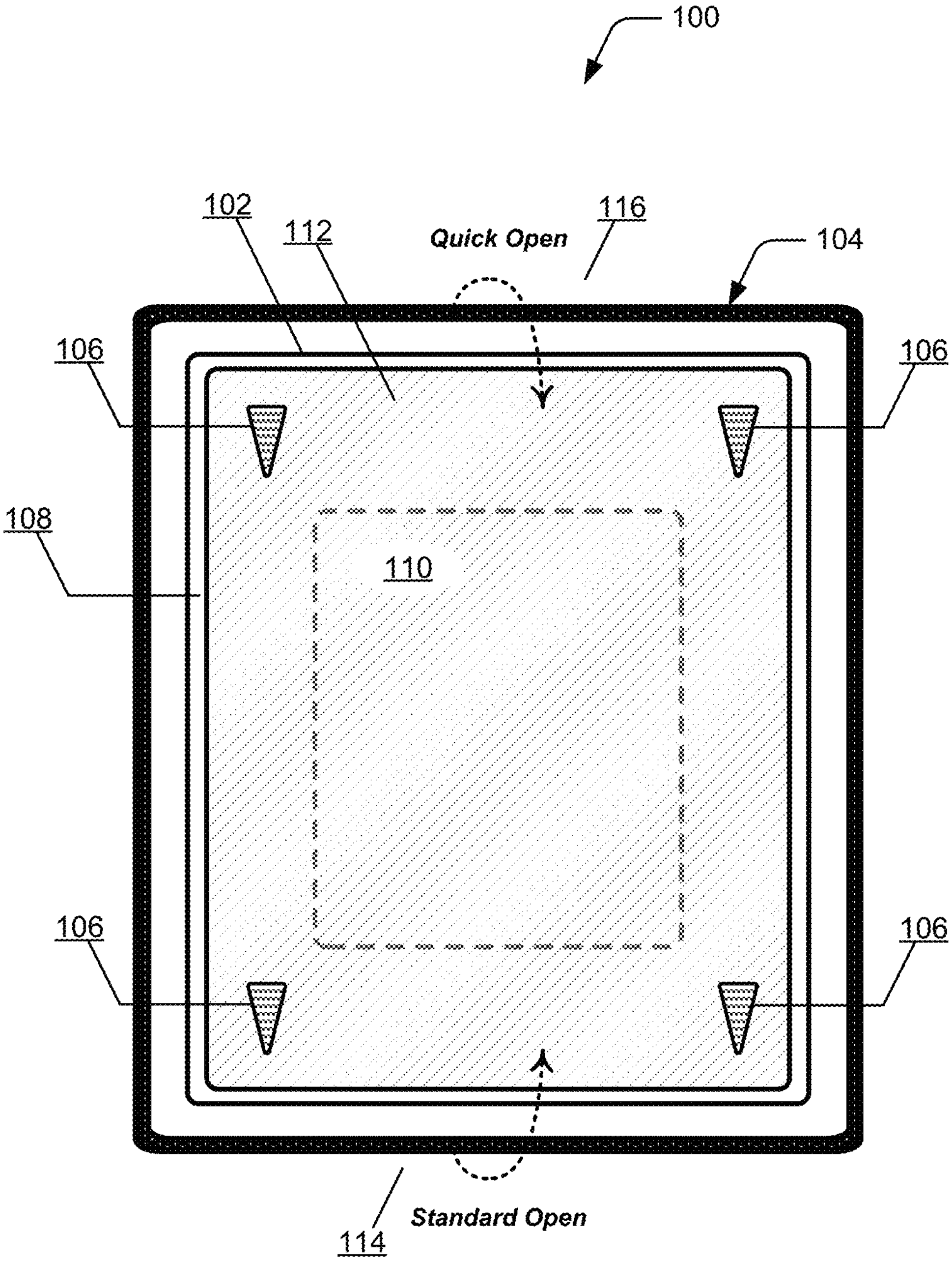
FIG. 1 illustrates an example of a bi-directional packaging adhesive in accordance with one or more implementations as described herein.

Implementations of a bi-directional packaging adhesive are described, and provides for both standard and quick opening packaging. In implementations, the design maintains the standard use of bandage packaging, while also providing for a quick opening option of the packaging for faster and simplified bandage application. Generally, with use of the bi-directional packaging adhesive, the packaging of any adhesive-type bandage or patch can be opened from different directions. When a bandage is opened in one direction, it opens as a consumer might expect a standard bandage to open, removing the packaging from around the bandage. The user can then remove the non-stick backing from the adhesive portion of the bandage and apply the bandage, such as on a person's skin over an injury. Alternatively, when the bandage is opened in an opposite direction, the bi-directional adhesive holds to the non-stick backing of the bandage, removing the non-stick backing from the bandage along with removing the packaging from around the bandage. The bandage is then ready for use and the user can quickly apply the bandage as needed.

Notably, the packaging design described herein using the bi-directional adhesive may also be implemented in similar concept for any type of easy-opening applications other than bandages, including but not limited to adhesives, surgical instruments, medical requisites, veterinary supplies, catering supplies, horticultural consumables, cosmetics, and any other type of items that are generally packaged for use in a clean and sterile environment. Further, an adhesive patch encompassed by the packaging may be any type of an adhesive-backed bandage, patch or pad, medicated patch, electrode or other monitor adhesives, and/or any other type of an adhesive-type patch that is designed to adhere to an applied surface, such as a person's skin.

In aspects of the described bi-directional packaging adhesive, an adhesive patch is sealed in packaging that utilizes the bi-directional packaging adhesive. The adhesive patch has an adhesive strip and a sterile pad, as well as a non-stick backing that adheres to the adhesive strip and covers the sterile pad. The non-stick backing is removable from the adhesive strip for application of the sterile pad and the adhesive strip of the adhesive patch. In implementations, the non-stick backing may be a one-piece backing that extends a full length and width of the adhesive strip inside of a sterile cavity formed by the sealed packaging around the adhesive patch. Alternatively, the non-stick backing may be a two-piece backing with a first piece of the non-stick backing overlapping a second piece of the non-stick backing to cover the sterile pad inside of the sterile cavity formed by the sealed packaging around the adhesive patch.

Generally, the packaging is sealed with a packaging adhesive forming the sterile cavity that encompasses the adhesive patch and the non-stick backing that adheres to the adhesive strip of the adhesive patch. In implementations, the packaging is designed for opening from either end, and generally the packaging is formed from two halves, sealed along the outer edges with the packaging adhesive. The packaging may be marked with exterior indications that clearly guide a user on the package opening options, such as to standard open the packaging or quick open the packaging.

The bi-directional adhesive is used to attach portions (or areas, regions) of the non-stick backing and/or the adhesive strip to the inside of the packaging. The bi-directional adhesive can be stamped in the shape of a triangle or wedge so that the packaging tears off easily in one direction, and holds firm when pulled in the opposite direction. The shape or thickness of the adhesive stamp makes the bi-directional adhesive intentionally weak in one direction, and strong in the opposite direction. Notably, the bi-directional adhesive releases from the inside of the packaging in a first package opening direction to remove the packaging from around the adhesive patch, yet maintains the adherence of the non-stick backing to the adhesive patch. Generally, opening the package from a "standard open" end in the first package opening direction separates a first or top half of the packaging from the second or bottom half of the packaging.

Additionally, the bi-directional adhesive is implemented to hold to the inside of the packaging in a second package opening direction to remove the non-stick backing from the adhesive patch along with removing the packaging from around the adhesive patch. The attached portions of the non-stick backing that are attached to the inside of the packaging by the bi-directional adhesive are configured to peel the non-stick backing from the adhesive patch in the second package opening direction to open the packaging. Generally, opening the package from a "quick open" end in the second package opening direction separates the first or top half of the packaging from the second or bottom half of the packaging, and also removes the non-stick backing from the adhesive patch. The non-stick backing being removed from the adhesive patch along with the packaging in the second package opening direction configures the adhesive patch for quick application.

In implementations, the bi-directional adhesive is approximately triangular or wedge-shaped, having a wide end tapering down to a narrow end, and/or may taper in thickness. The first package opening direction ("standard open") detaches the bi-directional adhesive from the inside of the packaging when moving in a direction from the narrow end to the wide end of the triangular or wedge-shaped bi-directional adhesive. This allows the non-stick backing to maintain its adherence on the adhesive patch while removing the packaging from around the adhesive patch. The second package opening direction ("quick open") allows for a stronger bi-directional adhesive bond with the inside of the packaging when moving in a direction from the wide end to the narrow end of the triangular or wedge-shaped bi-directional adhesive. This removes the non-stick backing from the adhesive patch along with removing the packaging from around the adhesive patch.

While features and concepts of bi-directional packaging adhesive can be implemented in any number of different environments and/or configurations, implementations of bi-directional packaging adhesive are described in the context of the following example descriptions and methods.

FIG. 1 illustrates an example 100 of an adhesive patch 102 sealed in packaging 104, and utilizing bi-directional packaging adhesive 106, as described herein. In this example 100, the adhesive patch 102 may be designed as any type of an adhesive-backed bandage, patch or pad, medicated patch, electrode or other monitor adhesives, and/or any other type of an adhesive-type patch that is designed to adhere to an applied surface, such as a person's skin. Generally, and adhesive patch or adhesive-backed bandage is usable in a multitude of environments for injury mitigation and/or as a skin or injury covering.

The adhesive patch 102 has an adhesive strip 108 and a sterile pad 110, as well as a non-stick backing 112 that adheres to the adhesive strip 108 and covers the sterile pad. The non-stick backing 112 is removable from the adhesive strip 108 for application of the sterile pad 110 and the adhesive strip of the adhesive patch. In implementations, the non-stick backing 112 may be a one-piece backing that extends a full length and width of the adhesive strip 108 inside of a sterile cavity formed by the sealed packaging 104 around the adhesive patch. Alternatively, the non-stick backing 112 may be a two-piece backing with a first piece of the non-stick backing overlapping a second piece of the non-stick backing to cover the sterile pad 110 inside of the sterile cavity formed by the sealed packaging 104 around the adhesive patch. Generally, the packaging 104 is sealed with a packaging adhesive forming the sterile cavity that encompasses the adhesive patch 102 and the non-stick backing 112 that adheres to the adhesive strip 108 of the adhesive patch.

In implementations, the packaging 104 is designed for opening from either end, and generally the packaging is formed from two halves, sealed along the outer edges with the packaging adhesive. The bi-directional adhesive 106 is used to attach portions (or areas, regions) of the non-stick backing 112 and/or the adhesive strip 108 to the inside of the packaging 104. The bi-directional adhesive 106 is implemented to release from the inside of the packaging 104 in a first package opening direction 114 to remove the packaging 104 from around the adhesive patch 102, yet maintain the adherence of the non-stick backing 112 to the adhesive patch. Generally, opening the package from the "standard open" end in the first package opening direction 114 separates a first or top half of the packaging from the second or bottom half of the packaging.

Additionally, the bi-directional adhesive 106 is implemented to hold to the inside of the packaging 104 in a second package opening direction 116 to remove the non-stick backing 112 from the adhesive patch 102 along with removing the packaging from around the adhesive patch. The attached portions of the non-stick backing 112 that are attached to the inside of the packaging 104 by the bi-directional adhesive 106 are configured to peel the non-stick backing 112 from the adhesive patch 102 in the second package opening direction 116 to open the packaging. Generally, opening the package from the "quick open" end in the second package opening direction 116 separates the first or top half of the packaging from the second or bottom half of the packaging, and also removes the non-stick backing 112 from the adhesive patch 102. The non-stick backing 112 being removed from the adhesive patch 102 along with the packaging 104 in the second package opening direction 116 configures the adhesive patch for quick application.

In implementations, the bi-directional adhesive 106 is approximately triangular or wedge-shaped, having a wide end tapering down to a narrow end. The first package opening direction 114 ("standard open") detaches the bi-directional adhesive 106 from the inside of the packaging 104 when moving in a direction from the narrow end to the wide end of the triangular or wedge-shaped bi-directional adhesive. As noted above, this allows the non-stick backing to maintain its adherence on the adhesive patch 102 while removing the packaging 104 from around the adhesive patch. The second package opening direction 116 ("quick open") allows for a stronger bi-directional adhesive bond with the inside of the packaging 104 when moving in a direction from the wide end to the narrow end of the triangular or wedge-shaped bi-directional adhesive. As noted above, this removes the non-stick backing 112 from the adhesive patch 102 along with removing the packaging 104 from around the adhesive patch.

Figure 2:
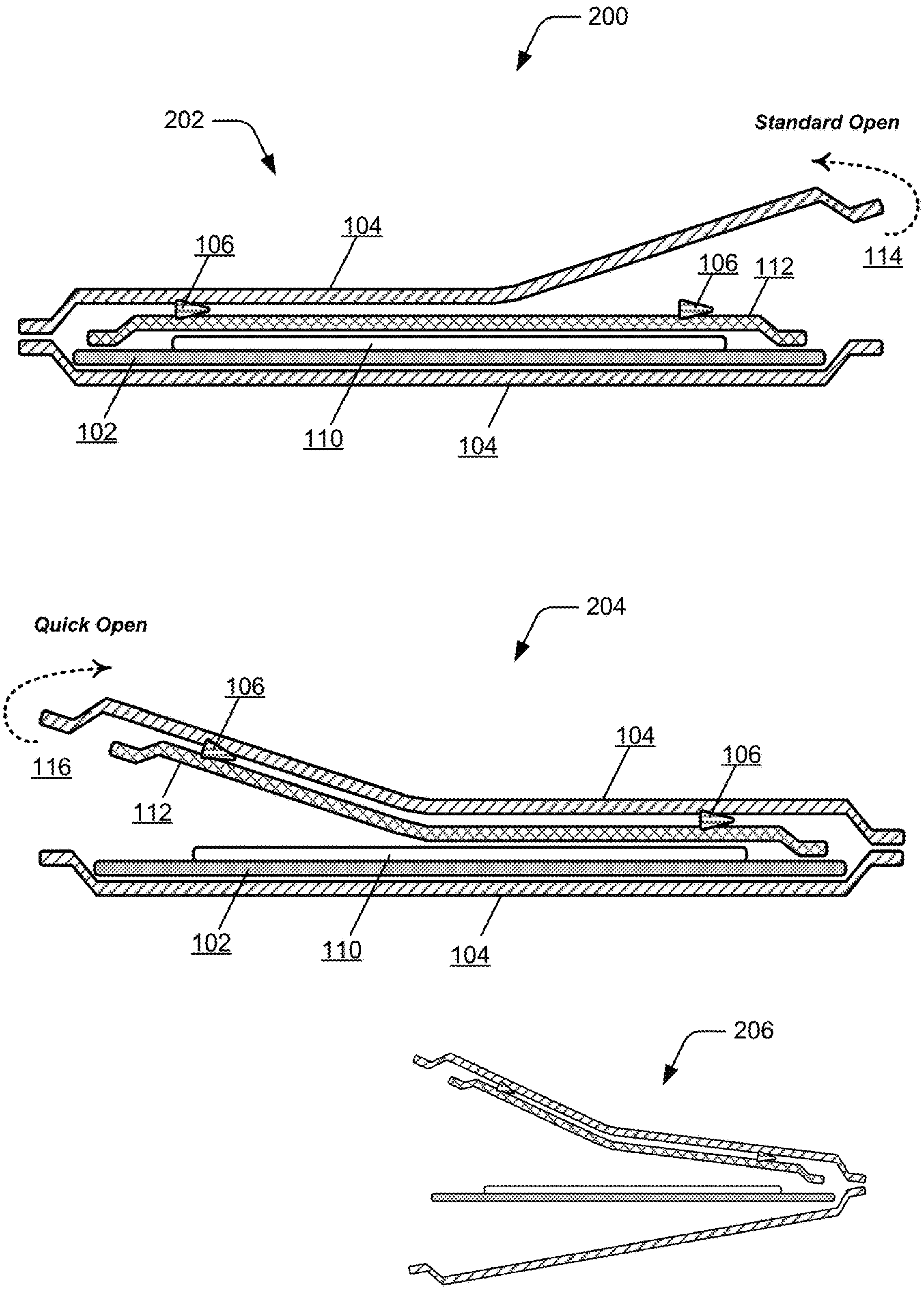
FIGS. 2-4 illustrate examples of additional aspects and features of the bi-directional packaging adhesive in accordance with one or more implementations as described herein.

FIG. 2 further illustrates an example 200 of additional features of the bi-directional packaging adhesive, as described herein. In this example 200, the adhesive patch 102 and the packaging 104 are shown in a side view 202. The bi-directional adhesive 106 releases from the inside of the packaging 104 in the first package opening direction 114 to remove the packaging 104 from around the adhesive patch 102, yet allows the non-stick backing 112 to maintain its adherence to the adhesive patch. The first package opening direction 114 ("standard open") detaches the bi-directional adhesive 106 from the inside of the packaging 104 when moving in a direction from the narrow end to the wide end of the triangular or wedge-shaped bi-directional adhesive. This allows the non-stick backing 112 to maintain its adherence on the adhesive patch 102 while removing the packaging 104 from around the adhesive patch.

As further shown in the side view 204, the bi-directional adhesive 106 holds to the inside of the packaging 104 in the second package opening direction 116 to remove the non-stick backing 112 from the adhesive patch 102 along with removing the packaging from around the adhesive patch. The attached portions of the non-stick backing 112 that are attached to the inside of the packaging 104 by the bi-directional adhesive 106 are configured to peel the non-stick backing 112 from the adhesive patch 102 in the second package opening direction 116 to open the packaging. The second package opening direction 116 ("quick open") allows for a stronger bi-directional adhesive bond with the inside of the packaging 104 when moving in a direction from the wide end to the narrow end of the triangular or wedge-shaped bi-directional adhesive. As shown at 206, this removes the non-stick backing 112 from the adhesive patch 102 along with removing the packaging 104 from around the adhesive patch.

Figure 3:
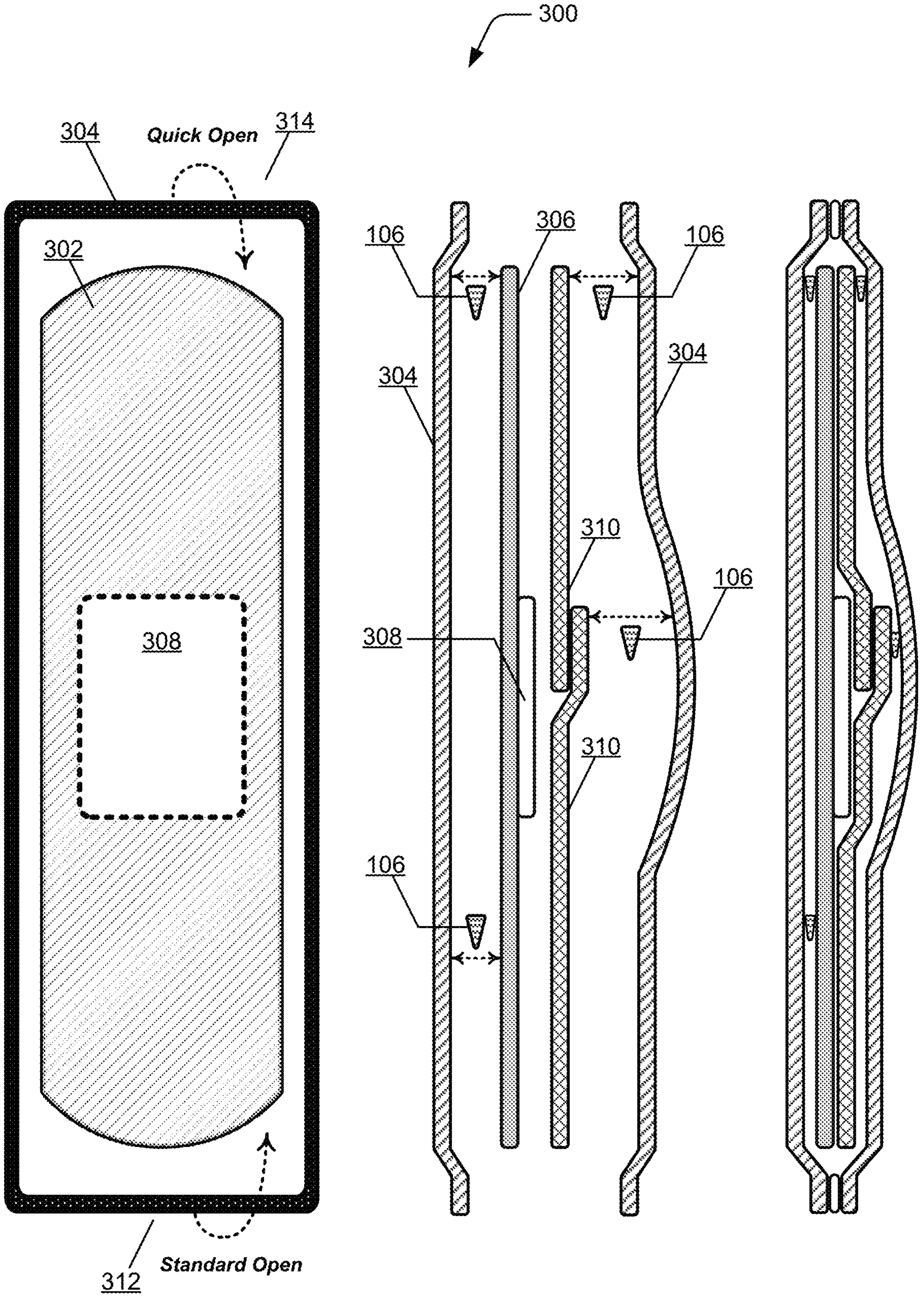

FIG. 3 further illustrates an example 300 of additional features of the bi-directional packaging adhesive, as described herein. In this example 300, an adhesive-type bandage 302 (e.g., an adhesive patch) is sealed in packaging 304, and utilizes the bi-directional packaging adhesive 106, such as shown and described with reference to FIGS. 1 and 2. The bandage 302 may be any adhesive-type patch or bandage that is designed to adhere to an applied surface, such as a person's skin. In this example 300, the bandage 302 is shown in a top view, a side view, and in an expanded side view.

The bandage 302 has an adhesive strip 306 and a sterile pad 308, as well as a non-stick backing 310 that adheres to the adhesive strip 306 and covers the sterile pad. The non-stick backing 310 is removable from the adhesive strip 306 for application of the sterile pad 308 and the adhesive strip 306 of the bandage. In implementations, the non-stick backing 310 may be a one-piece backing that extends a full length and width of the adhesive strip 306 inside of a sterile cavity formed by the sealed packaging 304 around the bandage. Alternatively, as shown in threshold example 300, the non-stick backing 310 may be a two-piece backing with a first piece of the non-stick backing overlapping a second piece of the non-stick backing to cover the sterile pad 308 inside of the sterile cavity formed by the sealed packaging 304 around the bandage. Generally, the packaging 304 is sealed with a packaging adhesive forming the sterile cavity that encompasses the bandage 302 and the non-stick backing 310 that adheres to the adhesive strip 306 of the bandage.

In implementations, the packaging 304 is designed for opening from either end, and generally the packaging is formed from two halves, sealed along the outer edges with the packaging adhesive. The bi-directional adhesive 106 is used to attach portions (or areas, regions) of the non-stick backing 310 and/or the adhesive strip 306 to the inside of the packaging 304. The bi-directional adhesive 106 is implemented to release from the inside of the packaging 304 in a first package opening direction 312 to remove the packaging 304 from around the bandage 302, yet maintain the adherence of the non-stick backing 310 to the bandage. Generally, opening the package from the "standard open" end in the first package opening direction 312 separates a first or top half of the packaging from the second or bottom half of the packaging.

Additionally, the bi-directional adhesive 106 is implemented to hold to the inside of the packaging 304 in a second package opening direction 314 to remove the non-stick backing 310 from the bandage 302 along with removing the packaging from around the bandage. The attached portions of the non-stick backing 310 that are attached to the inside of the packaging 304 by the bi-directional adhesive 106 are configured to peel the overlapping two-piece non-stick backing 310 from the bandage 302 in the second package opening direction 314 to open the packaging. Generally, opening the package from the "quick open" end in the second package opening direction 314 separates the first or top half of the packaging from the second or bottom half of the packaging, and also removes the non-stick backing 310 from the bandage 302. The non-stick backing 310 being removed from the bandage 302 along with the packaging 304 in the second package opening direction 314 configures the bandage for quick application.

In implementations, the bi-directional adhesive 106 is approximately triangular or wedge-shaped, having a wide end tapering down to a narrow end. The first package opening direction 312 ("standard open") detaches the bi-directional adhesive 106 from the inside of the packaging 304 when moving in a direction from the narrow end to the wide end of the triangular or wedge-shaped bi-directional adhesive. As noted above, this allows the non-stick backing 310 to maintain its adherence on the bandage 302 while removing the packaging 304 from around the bandage. The second package opening direction 314 ("quick open") allows for a stronger bi-directional adhesive bond with the inside of the packaging 304 when moving in a direction from the wide end to the narrow end of the triangular or wedge-shaped bi-directional adhesive. As noted above, this removes the overlapping two-piece non-stick backing 310 from the bandage 302 along with removing the packaging 304 from around the bandage.

Figure 4:
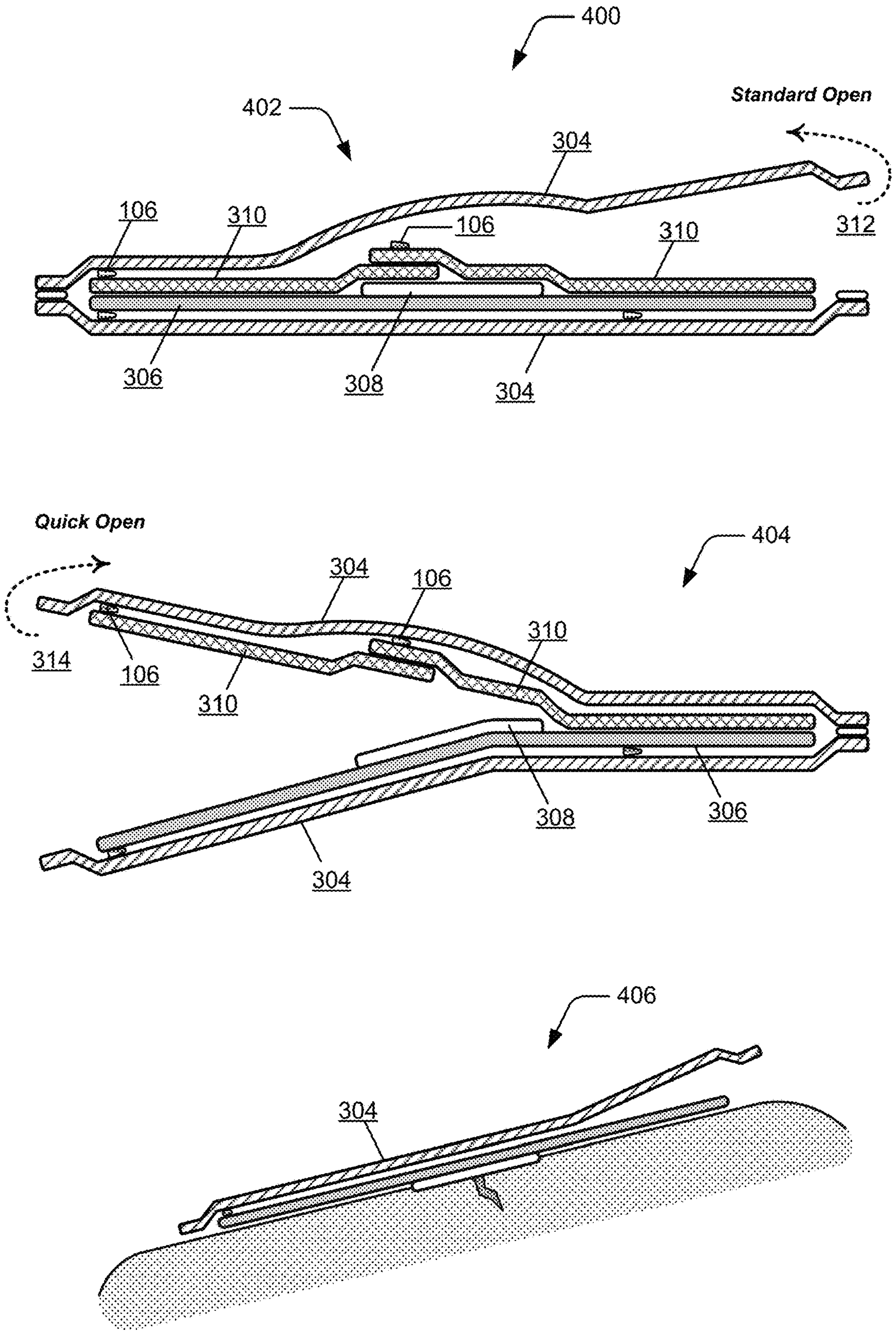

FIG. 4 further illustrates an example 400 of additional features of the bi-directional packaging adhesive, as described herein. In this example 400, the bandage 302 and the packaging 304 are shown in a side view 402. The bi-directional adhesive 106 releases from the inside of the packaging 304 in the first package opening direction 312 to remove the packaging 304 from around the bandage 302, yet allows the non-stick backing 310 to maintain its adherence to the bandage. The first package opening direction 312 ("standard open") detaches the bi-directional adhesive 106 from the inside of the packaging 304 when moving in a direction from the narrow end to the wide end of the triangular or wedge-shaped bi-directional adhesive. This allows the non-stick backing 310 to maintain its adherence on the bandage 302 while removing the packaging 304 from around the bandage.

As further shown in the side view 404, the bi-directional adhesive 106 holds to the inside of the packaging 304 in the second package opening direction 314 to remove the non-stick backing 310 from the bandage 302 along with removing the top half of the packaging from around the bandage. The attached portions of the non-stick backing 310 that are attached to the inside of the packaging 304 by the bi-directional adhesive 106 are configured to peel the non-stick backing 310 from the bandage 302 in the second package opening direction 314 to open the packaging. The second package opening direction 314 ("quick open") allows for a stronger bi-directional adhesive bond with the inside of the packaging 304 when moving in a direction from the wide end to the narrow end of the triangular or wedge-shaped bi-directional adhesive. This removes the non-stick backing 310 from the bandage 302 along with removing the top half of the packaging 304 from around the bandage.

As further shown at 406, the sterile pad 308 can be adhered in place with the adhesive strip 306, such as over an injury to a user's skin, and the adhesive strip 306 holds the sterile pad 308 in place. Notably in this example, the lower half of the packaging 304 remains attached to the bandage by the bi-directional adhesive 106 when the package is opened in the second package opening direction 314 ("quick open"). This provides that a user can apply the bandage without contaminating or inadvertently contacting the sterile pad or the adhesive strip of the bandage. After the application of the sterile pad 308 with the adhesive strip 306, the remaining lower half of the packaging can simply be pulled off and separated from the now applied bandage. The design of the bi-directional adhesive allows direct application of the bandage itself, and after placement of the bandage, the remaining exterior packaging can be easily removed. This design allows the sterile field of the bandage to be maintained, and the bandage can be applied without a user ever having to touch the sterile pad or the adhesive strip of the bandage.

Figure 5:
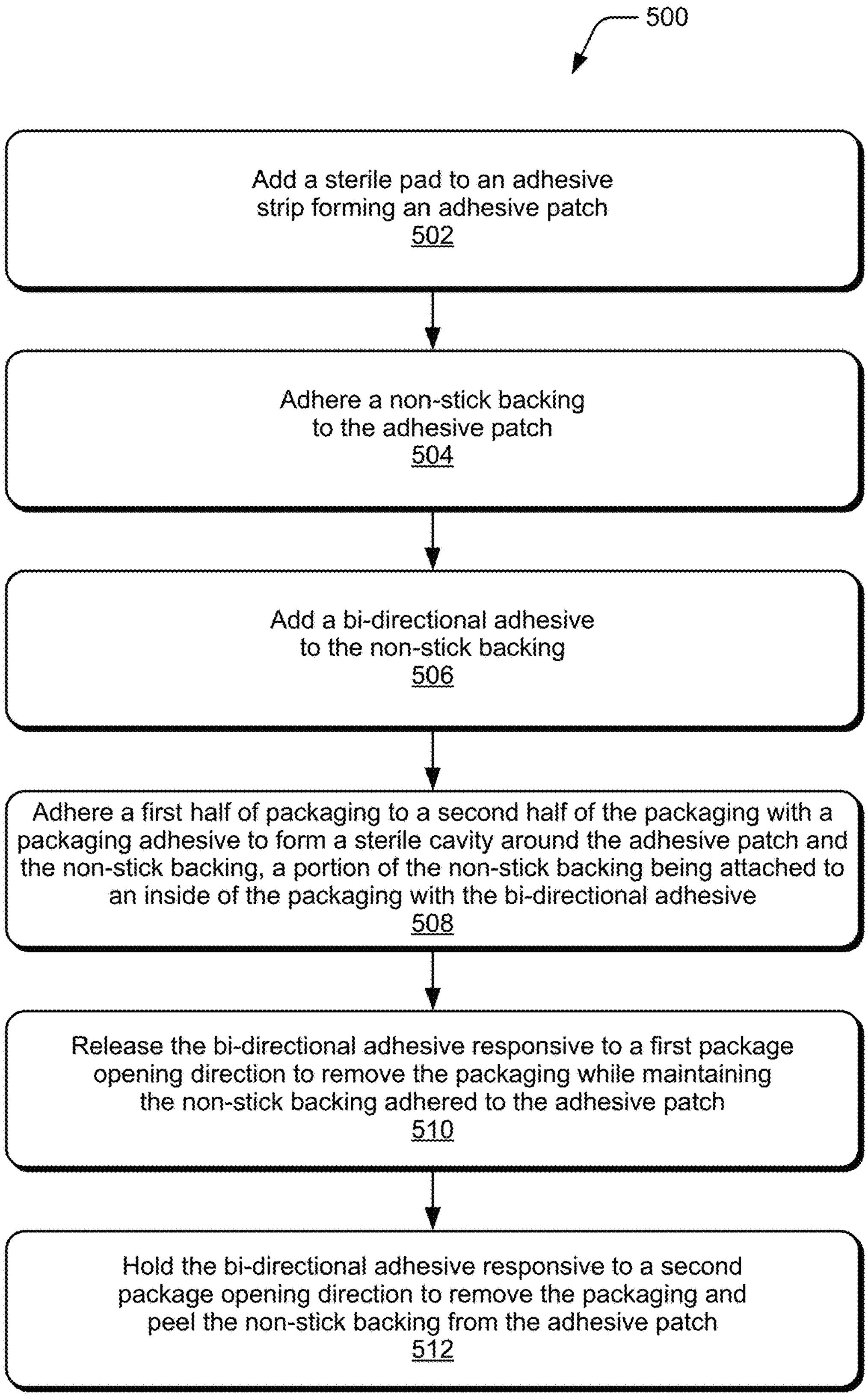
FIGS. 5 and 6 illustrate example methods of a bi-directional packaging adhesive in accordance with one or more implementations of the techniques described herein.

FIG. 5 illustrates example method(s) 500 of a bi-directional packaging adhesive. The order in which the method is described is not intended to be construed as a limitation, and any number or combination of the described method operations can be performed in any order to perform a method, or an alternate method.

At 502, a sterile pad is added to an adhesive strip forming an adhesive patch. For example, the sterile pad 110 is added, attached, or otherwise adhered to the adhesive strip 108, forming the adhesive patch 102. Similarly, the sterile pad 308 is added, attached, or otherwise adhered to the adhesive strip 306, forming the bandage 302.

At 504, a non-stick backing is adhered to the adhesive patch. For example, the non-stick backing 112 is adhered to the adhesive patch 102 and covers the sterile pad 110 of the adhesive patch 102. In implementations, the non-stick backing 112 may be a one-piece backing that extends a full length and width of the adhesive strip 108 inside of a sterile cavity formed by the sealed packaging 104 around the adhesive patch. Similarly, the non-stick backing 310 is adhered to the adhesive strip 306 and covers the sterile pad 308 of the bandage 302. In implementations, the non-stick backing 310 may be a two-piece backing with a first piece of the non-stick backing overlapping a second piece of the non-stick backing to cover the sterile pad 308 inside of the sterile cavity formed by the sealed packaging 304 around the bandage.

At 506, bi-directional adhesive is added to the non-stick backing. For example, the bi-directional adhesive 106 is added to the non-stick backing 112 of the adhesive patch 102. Similarly, the bi-directional adhesive 106 is added to the non-stick backing 310 of the bandage 302.

At 508, a first half of packaging is adhered to a second half of the packaging with a packaging adhesive to form a sterile cavity around the adhesive patch and the non-stick backing, a portion of the non-stick backing being attached to an inside of the packaging with the bi-directional adhesive. For example, the packaging 104 of the adhesive patch 102 is formed from two halves, sealed along the outer edges with a packaging adhesive to form a sterile cavity that encompasses the adhesive patch 102 and the non-stick backing 112 that adheres to the adhesive strip 108 of the adhesive patch. The bi-directional adhesive 106 is used to attach portions (or areas, regions) of the non-stick backing 112 to the inside of the packaging 104 of the adhesive strip. Similarly, the packaging 304 of the bandage 302 is formed from two halves, sealed along the outer edges with a packaging adhesive to form a sterile cavity that encompasses the bandage 302 and the non-stick backing 310 that adheres to the adhesive strip 306 of the bandage. The bi-directional adhesive 106 is used to attach portions (or areas, regions) of the non-stick backing 310 to the inside of the packaging 304 of the bandage.

At 510, the bi-directional adhesive is released responsive to a first package opening direction to remove the packaging while maintaining the non-stick backing adhered to the adhesive patch. For example, the bi-directional adhesive 106 is implemented to release from the inside of the packaging 104 in a first package opening direction 114 to remove the packaging 104 from around the adhesive patch 102, yet maintain the adherence of the non-stick backing 112 to the adhesive patch. Similarly, the bi-directional adhesive 106 is implemented to release from the inside of the packaging 304 in a first package opening direction 312 to remove the packaging 304 from around the bandage 302, yet maintain the adherence of the non-stick backing 310 to the bandage.

At 512, the bi-directional adhesive holds responsive to a second package opening direction to remove the packaging and peel the non-stick backing from the adhesive patch. For example, the bi-directional adhesive 106 is implemented to hold to the inside of the packaging 104 in a second package opening direction 116 to remove the non-stick backing 112 from the adhesive patch 102 along with removing the packaging from around the adhesive patch. Similarly, the bi-directional adhesive 106 is implemented to hold to the inside of the packaging 304 in a second package opening direction 314 to remove the non-stick backing 310 from the bandage 302 along with removing the packaging from around the bandage.

Figure 6:
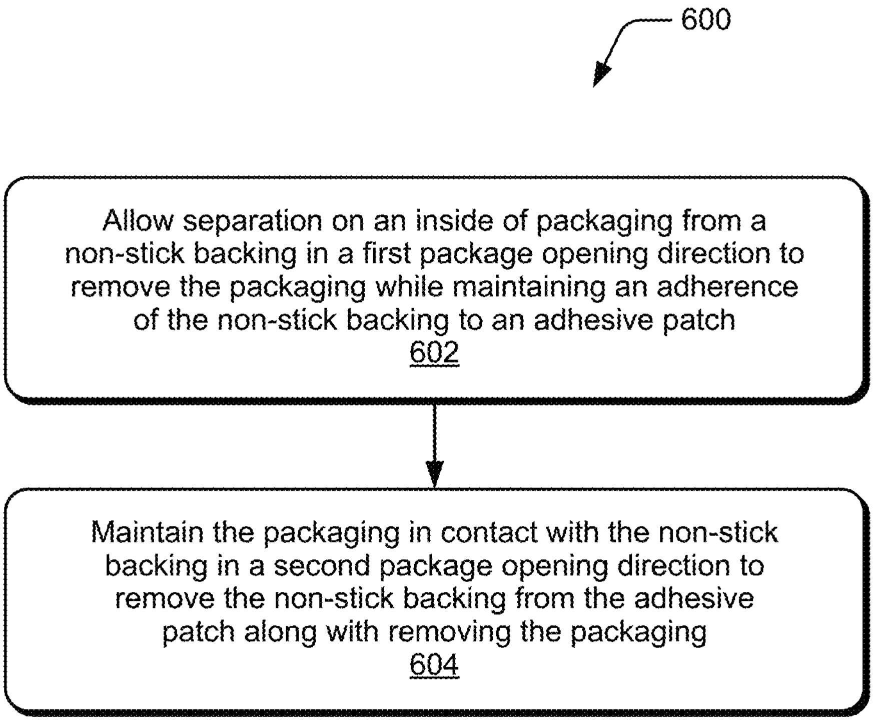

FIG. 6 illustrates an example method 600 of a bi-directional packaging adhesive. The order in which the method is described is not intended to be construed as a limitation, and any number or combination of the described method operations can be performed in any order to perform a method, or an alternate method.

At 602, separation on an inside of packaging from a non-stick backing in a first package opening direction is allowed to remove the packaging while maintaining an adherence of the non-stick backing to an adhesive patch. For example, the bi-directional adhesive 106 allows separation on an inside of the packaging 104 from the non-stick backing 112 in the first package opening direction 114 ("standard open") to remove the packaging while maintaining the adherence of the non-stick backing 112 to the adhesive patch 102.

At 604, the packaging is maintained in contact with the non-stick backing in a second package opening direction to remove the non-stick backing from the adhesive patch along with removing the packaging. For example, the bi-directional adhesive 106 maintains the packaging 104 in contact with the non-stick backing 112 in the second package opening direction 116 ("quick open") to remove the non-stick backing 112 from the adhesive patch 102 along with removing the packaging.

Production of novel bandage packaging design with described methods, and other methods known in the art, are described with reference to FIGS. 7-12.

Figure 7:
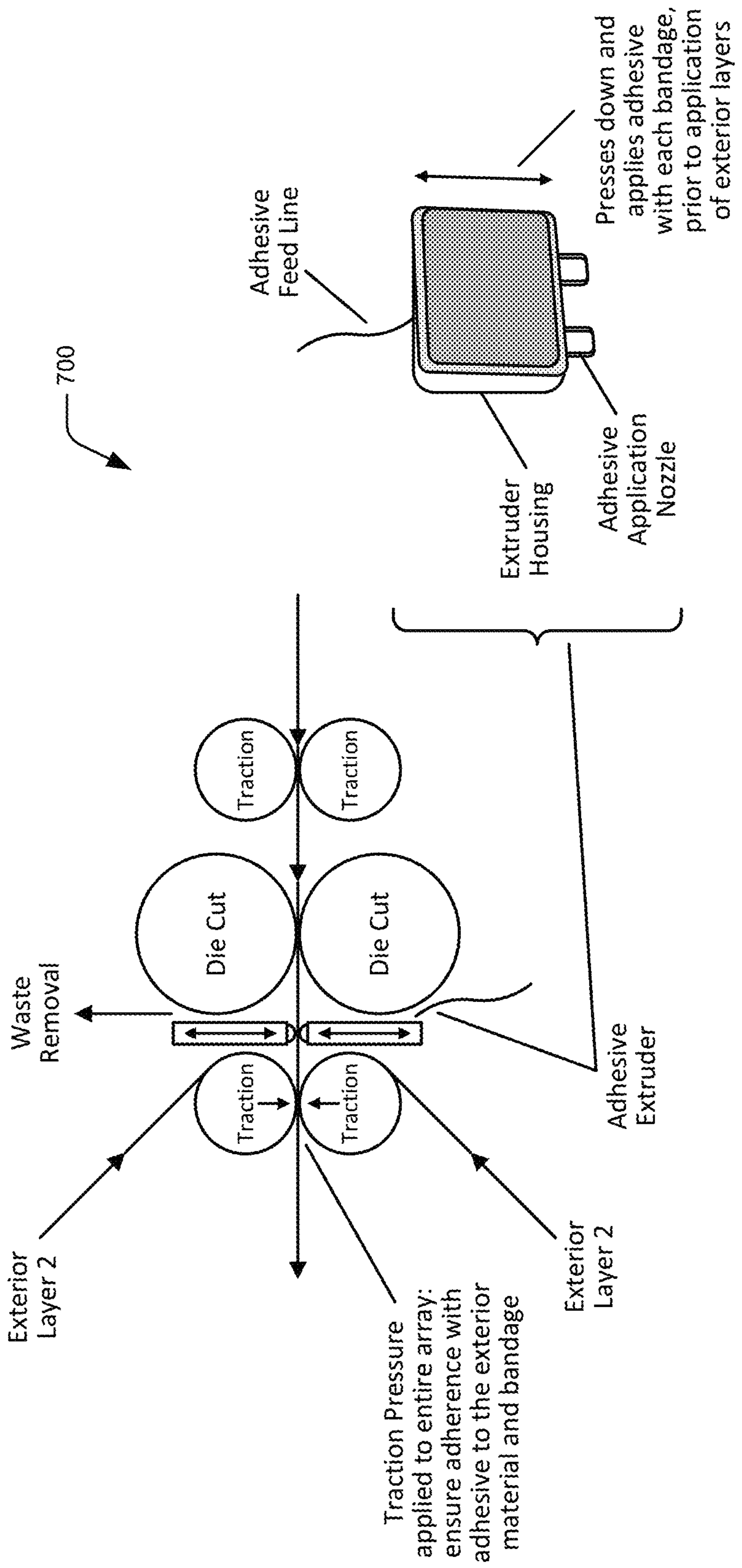
FIG. 7 illustrates an example of an extruder in a separate housing after die-cut roller, related to bi-directional packaging adhesive as described herein.

FIG. 7 illustrates an example 700 of an extruder in a separate housing after die-cut roller, as related to bi-directional packaging adhesive as described herein. In an implementation, the adhesive is applied with a stamp-press. The press moves down and applies the adhesive to the surface of the bandage, or to the exterior packaging, and then returns to a neutral position. The adhesive is pressed by another set of rollers which applies pressure to the top and bottom of the package, securing an adherence of the adhesive placement.

Figure 8:
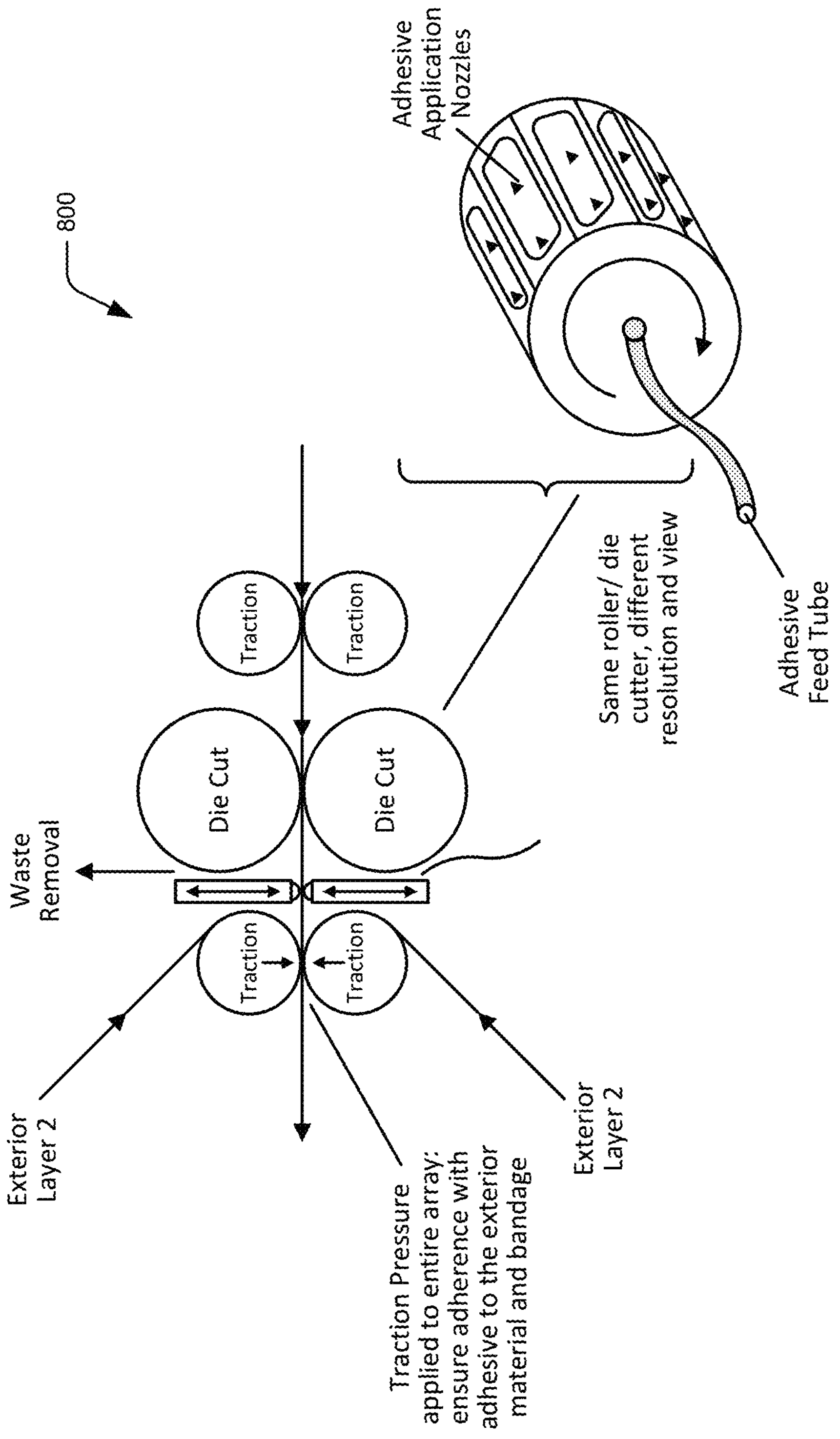
FIG. 8 illustrates an example of an extruder within a roller, related to bi-directional packaging adhesive as described herein.

FIG. 8 illustrates an example 800 of an extruder within a roller, as related to bi-directional packaging adhesive as described herein. In an implementation, a roller with built-in extruders for adhesive placement applies the adhesive, just prior to being placed between the bottom and top exterior packaging pieces. After placed between the exterior packaging pieces, the whole bandage is passed through two or more wheels that apply force to the top and bottom of the bandage, cementing the novel adhesive placement to the bandage and its associated exterior piece, and the non-stick peel off portion to its associated exterior piece. The roller may be placed to apply directly onto the bandage, or onto the exterior layers prior to joining materials.

Figure 9:
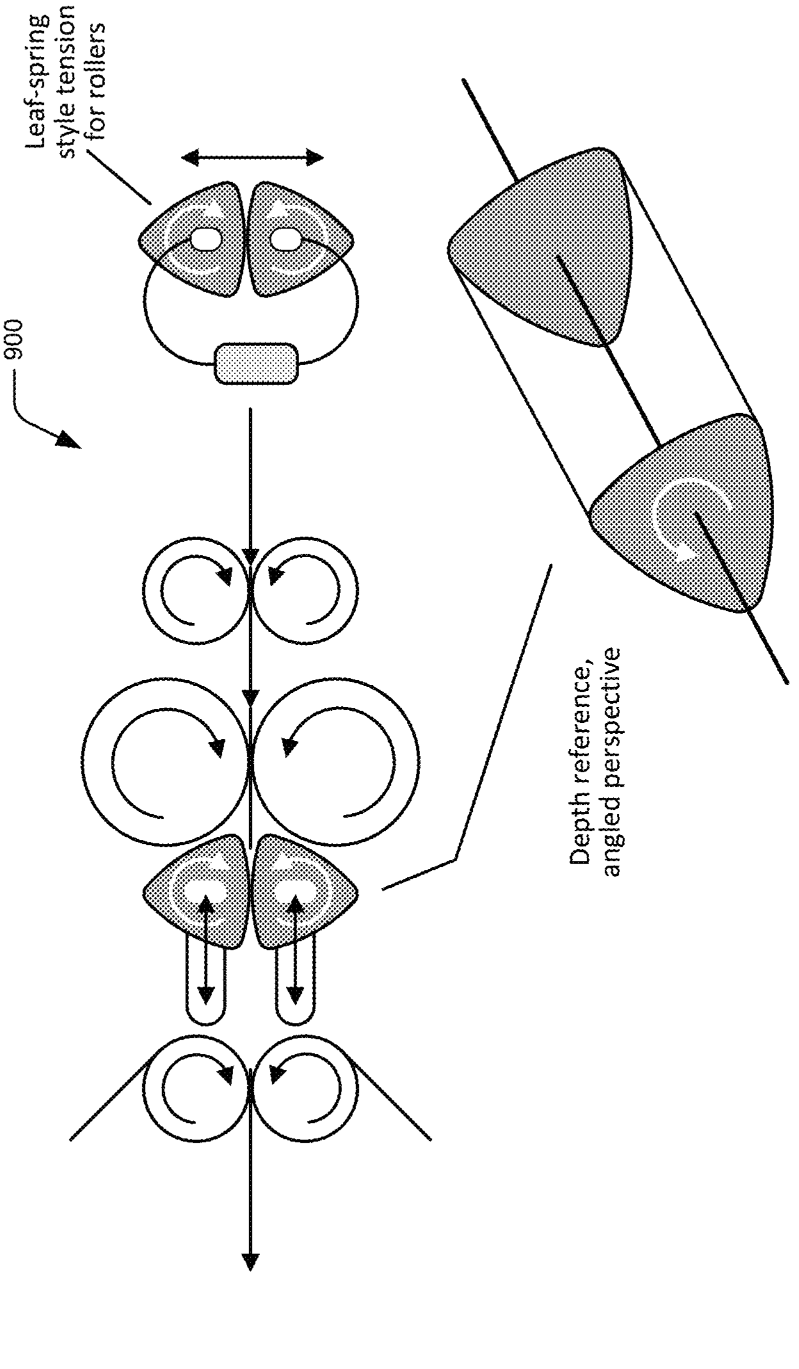
FIG. 9 illustrates an example of transfer and extrusion with Reuleaux triangle rollers, related to bi-directional packaging adhesive as described herein.

FIG. 9 illustrates an example 900 of transfer and extrusion with Reuleaux triangle rollers, as related to bi-directional packaging adhesive as described herein. Utilizing the curved aspects of the Reuleaux triangle to grasp an edge of the die-cut bandage, and the rocking motion to both apply extruded adhesive material and transition to a final addition of exterior layers, this aspect applies a side to side and rotating motion (stationary, or back and forth movement as required). If stationary, two leaf-springs or tensioners could allow the triangle rollers to oscillate as needed to perform the task of transfer and application of adhesive.

Figure 10:
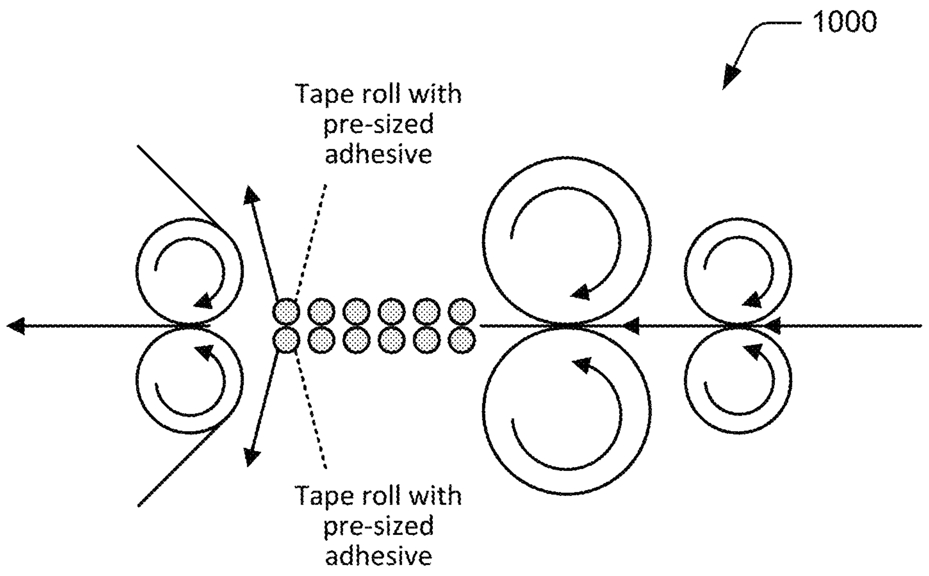
FIG. 10 illustrates an example of a series of small rollers, related to bi-directional packaging adhesive as described herein.

FIG. 10 illustrates an example 1000 of a series of small rollers, as related to bi-directional packaging adhesive as described herein. To maintain control of the die-cut bandage during transfer to exterior layers application, a series of small, powered rollers may be used to propel the bandage as needed, with the final roller having an application of adhesive (either with in-roller extrusion, a separately-housed stamp method, or with the roll of tape with adhesives pre-applied).

Figure 11:
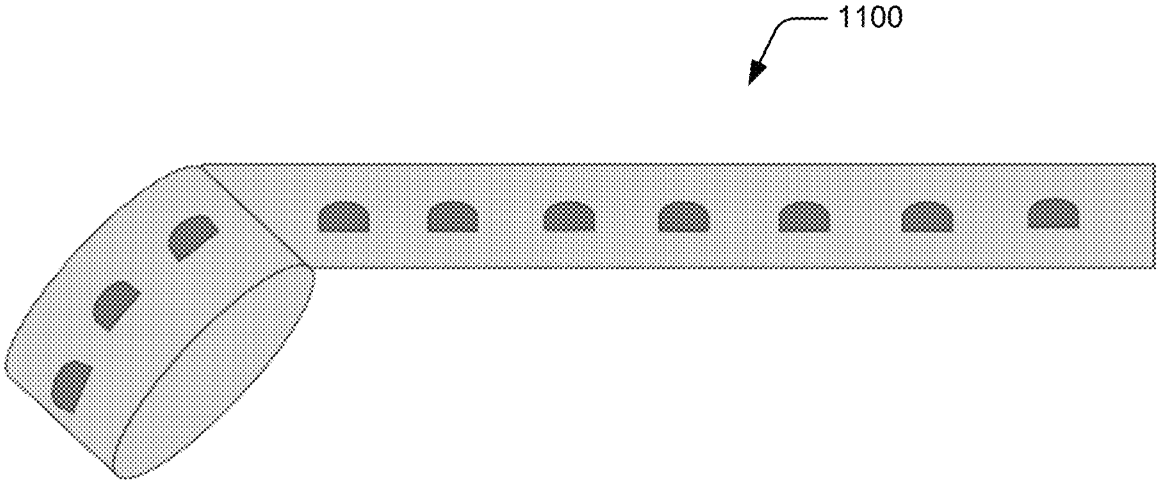
FIG. 11 illustrates an example of utilizing dots of adhesive on a pre-made roll of tape, related to bi-directional packaging adhesive as described herein

FIG. 11 illustrates an example 1100 of utilizing dots of adhesive on a pre-made roll of tape, as related to bi-directional packaging adhesive as described herein. A roll of tape with pre-measured and spaced adhesive dots, dispenses dots of adhesive material, and would allow for accurate measures of adhesive, placed at precise intervals. It would be added to a roller and either the tape could be re-used or could be disposed of appropriately.

Figure 12:
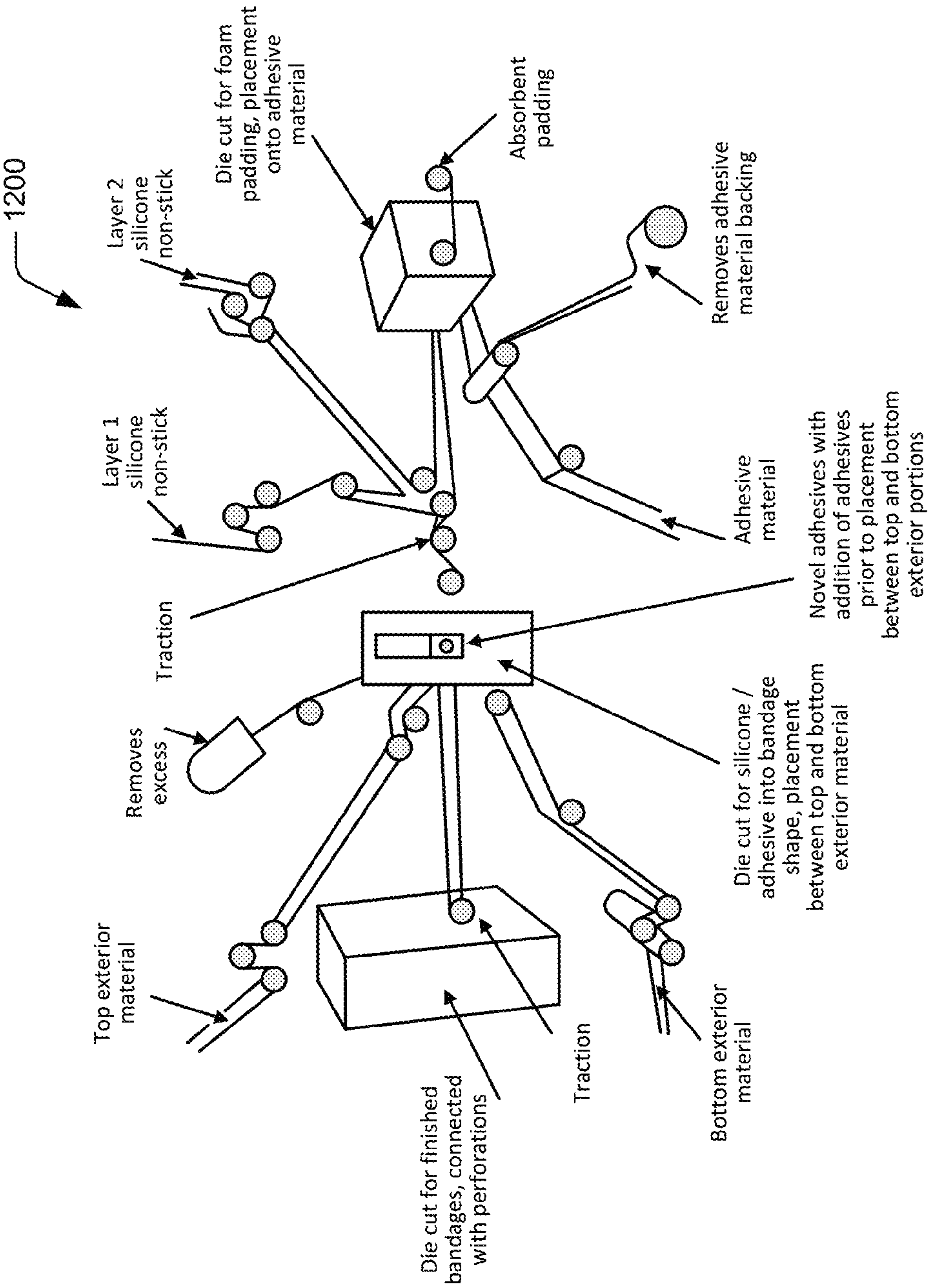
FIG. 12 illustrates an example of an adhesive bandage making machine, as related to bi-directional packaging adhesive as described herein.

FIG. 12 illustrates an example 1200 of suction-grasp transfer and line re-tooling, as related to bi-directional packaging adhesive as described herein. In an implementation, the die-cut bandages are moved between the top and bottom exterior layers with a vacuum-grasp transfer. With this technique, the adhesive can be applied enroute to the placement between the exterior layers via a roller-style applicator or a press-nozzle type application. Including but not limited to utilizing the large cutting surface (including an extruder for this technique), the vacuum-grasp aspect, or a combination of the two. Additionally, to add folds to both ends of a bandage, the exterior packaging can be pre-made in a fashion which has small folds at either end, allowing bi-directional application for a final product. Similarly, a small addition to the standard process could facilitate a fold on either end prior to the material being joined to other aspects of the production process.

Figure 13:
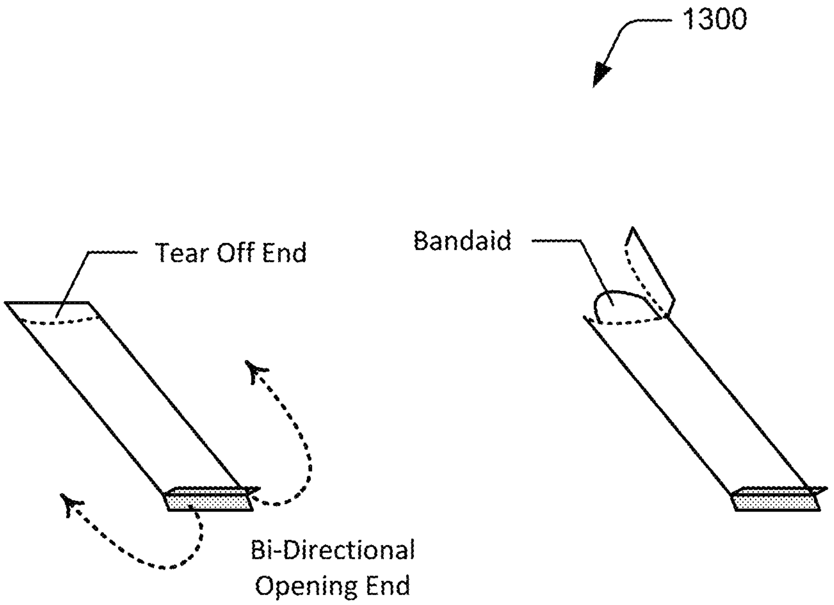
FIG. 13 illustrates an example of bandage packaging, related to bi-directional packaging adhesive as described herein.

FIG. 13 further illustrates an example 1300 of packaging (e.g., a bandage packaging) that opens as described herein from a bi-directional opening end, as well as having a packaging tear-off end.

Although implementations of a bi-directional packaging adhesive have been described in language specific to features and/or methods, the appended claims are not necessarily limited to the specific features or methods described. Rather, the specific features and methods are disclosed as example implementations of a bi-directional packaging adhesive, and other equivalent features and methods are intended to be within the scope of the appended claims. Further, various different examples are described and it is to be appreciated that each described example can be implemented independently or in connection with one or more other described examples. Additional aspects of the techniques, features, and/or methods discussed herein relate to one or more of the following claims.

The invention claimed is:

1. A sterile package, comprising:
- a bandage that includes a sterile pad, the bandage configured to adhere to an applied surface;
- a non-stick backing that adheres to the bandage, the non-stick backing being removable for application of the bandage;
- packaging that encompasses the bandage and the non-stick backing; and
- a bi-directional adhesive configured to:
  - release in a first package opening direction to remove the packaging while maintaining the adherence of the non-stick backing to the bandage; and
  - hold in a second package opening direction to remove the non-stick backing from the bandage along with removing the packaging.

2. The sterile package of claim 1, wherein a portion of the non-stick backing is attached to an inside of the packaging with the bi-directional adhesive, the attached portion configured to peel the non-stick backing from the bandage in the second package opening direction to open the packaging.

3. The sterile package of claim 1, wherein the non-stick backing being removed from the bandage along with the packaging in the second package opening direction configures the bandage for application.

4. The sterile package of claim 1, wherein:

the packaging is configured for opening from a first end or a second end of the packaging;

opening the packaging from the first end in the first package opening direction separates a first half of the packaging from a second half of the packaging; and opening the packaging from the second end in the second package opening direction separates the first half of the packaging from the second half of the packaging and removes the non-stick backing from the bandage.

5. The sterile package of claim 1, wherein:

the bi-directional adhesive allows separation of the packaging from the non-stick backing in the first package opening direction to remove the packaging while maintaining the adherence of the non-stick backing to the bandage; and the bi-directional adhesive maintains the packaging in contact with the non-stick backing in the second package opening direction to remove the non-stick backing from the bandage along with removing the packaging.

6. The sterile package of claim 1, wherein:

the bi-directional adhesive is triangular-shaped having a wide end tapering down to a narrow end;

the first package opening direction is from the narrow end to the wide end of the bi-directional adhesive, which maintains the adherence of the non-stick backing to the bandage while removing the packaging; and the second package opening direction is from the wide end to the narrow end of the bi-directional adhesive, which removes the non-stick backing from the bandage along with removing the packaging.

7. The sterile package of claim 1, wherein:

the bi-directional adhesive is wedge-shaped having a wide end tapering down to a narrow end;

the first package opening direction is from the narrow end to the wide end of the bi-directional adhesive, which maintains the adherence of the non-stick backing to the bandage while removing the packaging; and the second package opening direction is from the wide end to the narrow end of the bi-directional adhesive, which removes the non-stick backing from the bandage along with removing the packaging.

8. The sterile package of claim 1, wherein the non-stick backing adheres to the bandage and covers the sterile pad.

9. The sterile package of claim 1, wherein the packaging is sealed with a packaging adhesive forming a sterile cavity that encompasses the bandage and the non-stick backing that adheres to the bandage.

10. The sterile package of claim 9, wherein the non-stick backing is a one-piece backing that extends a full length and width of the bandage inside of the sterile cavity formed by the sealed packaging.

11. The sterile package of claim 9, wherein the non-stick backing is a two-piece backing with a first piece of the non-stick backing overlapping a second piece of the non-stick backing inside of the sterile cavity formed by the sealed packaging.

12. A bi-directional opening package, comprising:

packaging forming a sterile cavity that encompasses a bandage with a sterile pad and a non-stick backing that adheres to the bandage; and a bi-directional adhesive configured to:

release responsive to a first package opening direction to remove the packaging while maintaining the non-stick backing adhered to the bandage; and hold responsive to a second package opening direction to remove the packaging and the non-stick backing from the bandage.

13. The bi-directional opening package of claim 12, wherein a portion of the non-stick backing is attached to an inside of the packaging with the bi-directional adhesive, the attached portion configured to peel the non-stick backing from the bandage in the second package opening direction to open the packaging.

14. The bi-directional opening package of claim 12, wherein the non-stick backing being removed from the bandage along with the packaging in the second package opening direction configures the bandage for application.

15. The bi-directional opening package of claim 12, wherein:

the packaging is configured for opening from a first end or a second end of the packaging;

opening the packaging from the first end in the first package opening direction separates a first half of the packaging from a second half of the packaging; and opening the packaging from the second end in the second package opening direction separates the first half of the packaging from the second half of the packaging and removes the non-stick backing from the bandage.

16. The bi-directional opening package of claim 12, wherein:

the bi-directional adhesive allows separation of the packaging from the non-stick backing in the first package opening direction to remove the packaging while maintaining the adherence of the non-stick backing to the bandage; and the bi-directional adhesive maintains the packaging in contact with the non-stick backing in the second package opening direction to remove the non-stick backing from the bandage along with removing the packaging.

17. The bi-directional opening package of claim 12, wherein:

the bi-directional adhesive is shaped having a wide end tapering down to a narrow end;

the first package opening direction is from the narrow end to the wide end of the bi-directional adhesive, which maintains the adherence of the non-stick backing to the bandage while removing the packaging; and the second package opening direction is from the wide end to the narrow end of the bi-directional adhesive, which removes the non-stick backing from the bandage along with removing the packaging.

18. The bi-directional opening package of claim 12, wherein the non-stick backing adheres to the bandage and covers the sterile pad.

19. The bi-directional opening package of claim 12, wherein the packaging is sealed with a packaging adhesive forming the sterile cavity.

20. A method for a bi-directional opening package, the method comprising:

adhering a non-stick backing to a bandage that includes a sterile pad;

adding a bi-directional adhesive to the non-stick backing; and adhering a first half of packaging to a second half of the packaging with a packaging adhesive to form a sterile cavity around the bandage and the non-stick backing, a portion of the non-stick backing being attached to an inside of the packaging with the bi-directional adhesive that is configured for:

release responsive to a first package opening direction to remove the packaging while maintaining the non-stick backing adhered to the bandage; and hold responsive to a second package opening direction to remove the packaging and peel the non-stick backing from the bandage.

* * * * *